United States Patent [19]

Koseki et al.

[11] Patent Number: 4,946,999
[45] Date of Patent: Aug. 7, 1990

[54] NOVEL INTERMEDIATES FOR SYNTHESIS OF TRICHOSTATIC ACID OR TRICHOSTATIN A, AND PROCESSES FOR PREPARING TRICHOSTATIC ACID AND TRICHOSTATIN A

[75] Inventors: Koshi Koseki, Yokohama; Kenji Mori, Tokyo, both of Japan

[73] Assignee: Japan Tobacco Inc., Tokyo, Japan

[21] Appl. No.: 313,505

[22] Filed: Feb. 22, 1989

[30] Foreign Application Priority Data

Mar. 4, 1988 [JP] Japan .................. 63-49595

[51] Int. Cl.$^5$ .......................................... C07C 229/00
[52] U.S. Cl. .................................. 562/452; 556/413; 556/423; 562/459
[58] Field of Search ......................... 562/452

[56] References Cited

U.S. PATENT DOCUMENTS

| | | | |
|---|---|---|---|
| 3,867,434 | 2/1975 | Diamond | 562/452 X |
| 3,868,406 | 2/1975 | Siddall | 562/452 X |
| 4,218,378 | 8/1980 | Bundy | 562/452 X |
| 4,218,478 | 8/1980 | Omura | 424/324 |
| 4,243,819 | 1/1981 | Henrick et al. | 562/452 X |

FOREIGN PATENT DOCUMENTS 0199153 10/1986 European Pat. Off. ............ 424/324

OTHER PUBLICATIONS

The Total Synthesis of (±)-Trichostatin A, by Ian Fleming et al., *Tetrahedron*, vol. 39, No. 6, 1983, pp. 841–846.

Methoden Der Organishen Chemie (Houben–Weyl) vol. X/1, 1971, pp. 1229–1231 and 1271–1273.

*Primary Examiner*—Paul F. Shaver

[57] ABSTRACT

The present invention relates to a process for preparing trichostatic acid represented by the following formula [14]

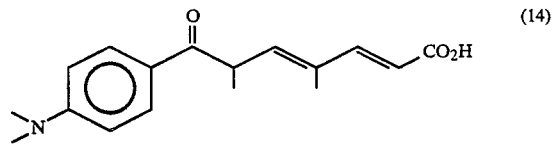

by oxidizing (E,E)-7-(4'-dimethylaminophenyl)-7-hydroxy-4,6-dimethylhepta-2,4-dienoic acid represented by the following formula [13]:

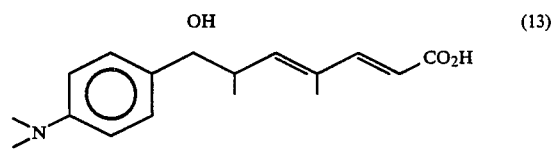

and a process for preparing trichostatin A represented by the following formula [15]:

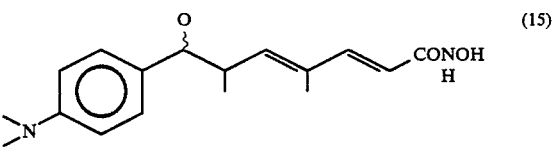

by allowing to react trichostatic acid with amine.

2 Claims, No Drawings

INTERMEDIATES FOR SYNTHESIS OF TRICHOSTATIC ACID OR TRICHOSTATIN A, AND PROCESSES FOR PREPARING TRICHOSTATIC ACID AND TRICHOSTATIN A

BACKGROUND OF THE INVENTION

The present invention relates to novel intermediates for synthesis of trichostatic acid represented by the following formula [14] or trichostatin A represented by the following formula [15], and processes for preparing trichostatic acid and trichostatin A, said trichostatic acid and trichostatin A being useful as an inducer for differentiating Friend cells (leukemia cells) of mouse.

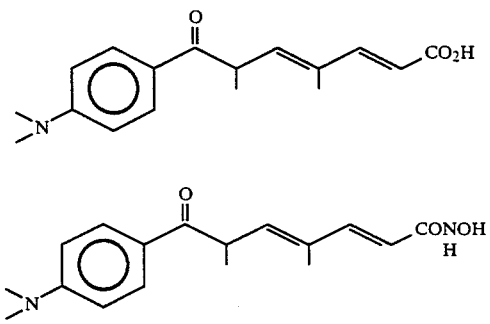

Trichostatic acid and trichostatin A (hereinafter these are referred to as trichostatins) were known as antibiotics, and in recent years, they have been found to be powerful inducer for differentiating cancer cells such as Friend cells [M. Yoshilda et al., Agric. Biol. Chem., 49, 563 (1985), Morioka et al., Abstract paper of the annula meeting (April 1985) of the Agricultural Chemical Society of Japan, page 221], and a study of trichostatins for cancer cells has become to give attention. Therefore, a study of trichostatins also has become to be an important theme.

Conventionally, trichlostantins have been prepared by the following two ways.

(a) Process using microorganisms

Extraction from liquid culture medium of micoorganisms such as Streptomyces hygroscopicus Y-50 [N. Tsuji et al., J. Antibiot. 29, 1 (1976)], Streptomyces sioyaensis ]H. Morioka et al., Agric. Biol. Chem, 49, 1365 (1985)] and Storeptomyces plantensis [M. Yoshida et al., Agric. Biol. Chem., 49, 563 (1985)]

(b) Synthesis by the processes of I. Fleming et al. [Tetrahedron, 39, 841 (1983)]

These processes of synthesis are shown below.

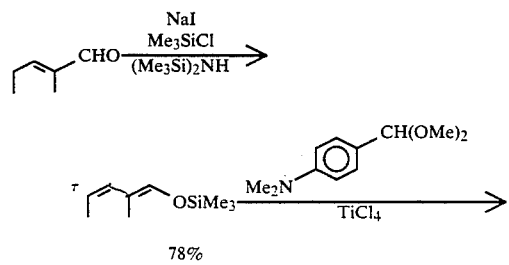

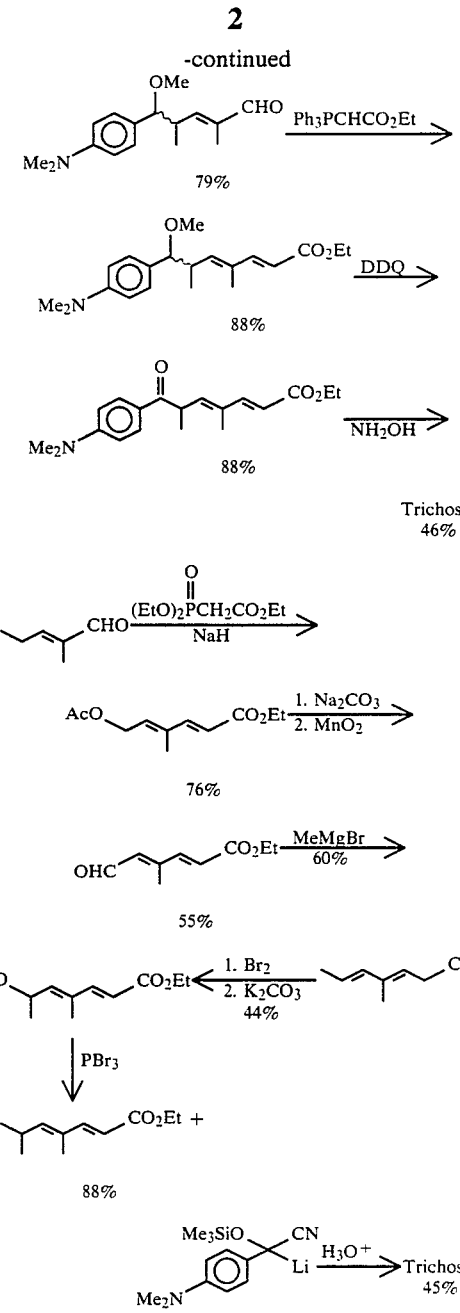

However, these conventional processes preparing trichostatins had several problems as shown in the following:

(a) In the microorganisms process

In this process, only single enantiomer may be obtained, but each enantiomers cannot be obtained.

Sometimes, production may not be steady owing to mutation of the strains.

Separation of trichostatic acid and trichostatin A is difficult in the step purifying the product from liquid culture medium.

(b) In the processes of I. Fleming et al.

Only racemic modification may be obtained, but optical active matter cannot be obtained.

In the conventional processes, optical active trichostatins of each enantiomers cannot be obtained.

3

Therefore, the study of cancer cells cannot be sufficiently performed when trichostatins obtained by the conventional processes are used. Consequently, optical active trichostatins of each enantiomers have been wanted to obtain.

We found that optical active trichostatins of each enantiomers can be obtained without remarkably losing optical purity of the starting material by using optical active methyl hydroxyisobutyrate as a starting material and synthesizing through the specified intermediates.

The present invention is based on this discovery.

SUMMARY OF THE INVENTION

The present invention relates to a process for preparing trichostatic acid represented by the following formula [14] by oxidizing (E,E)-7-(4'-dimethylaminophenyl)-7-hydroxy-4,6-dimethylhepta-2,4-dienoic acid represented by the following formula [13], and a process for preparing trichostatin A represented by the following formula [15] by oxidizing (E,E)-7-(4'-dimethylaminophenyl)-7-hydroxy-4,6-dimethylhepta-2,4-dienoic acid represented by the following formula [13], followed by reacting trichostatic acid thus obtained represented by the following formula [14] with amines, and further the present invention relates to novel intermediates for synthesis thereof.

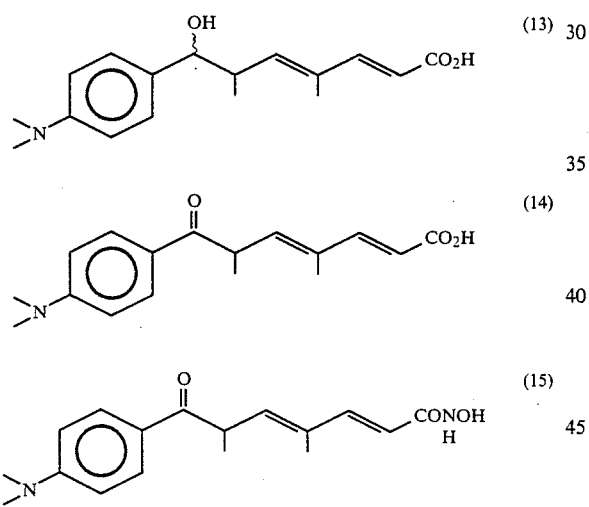

The compounds and the preparing processes according to the present invention are shown in the following reaction formulae. Compounds [2], [7] and [11] are well known.

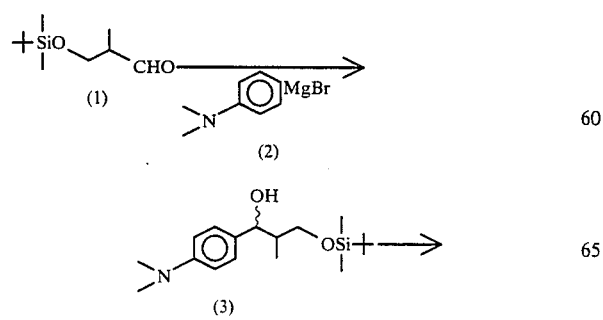

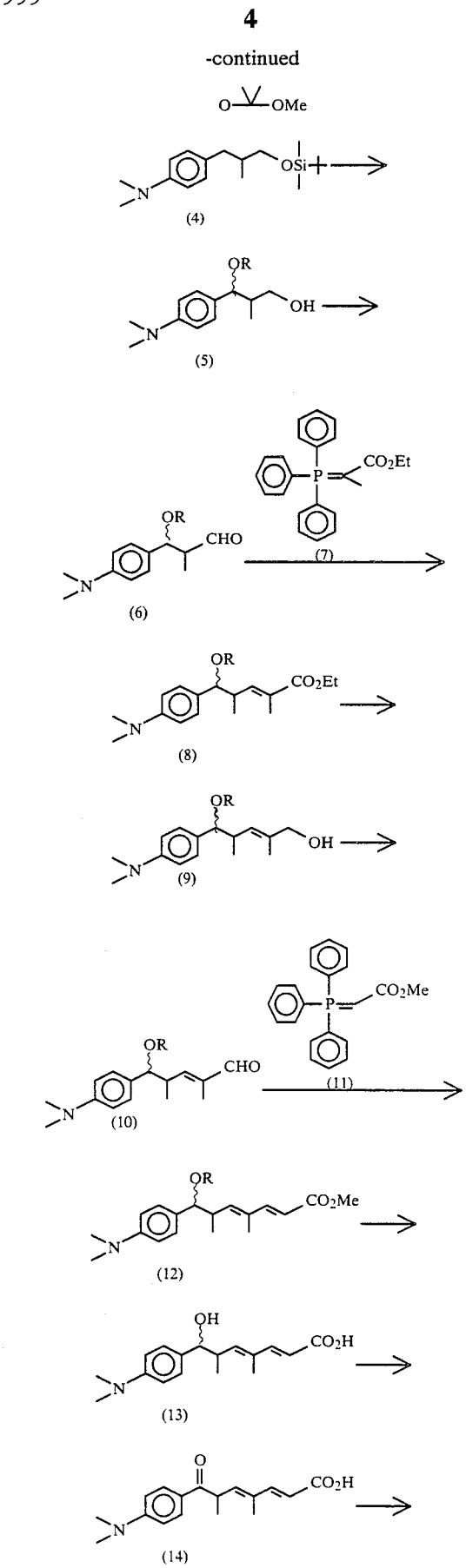

(15)

(In the above formulae, R designates a methoxypropyl group.)

The steps of the processes are explained in the following:

Compound [3] can be prepared by reacting aldehyde [1] with Grignard reagent [2] in a non-aqueous solvent at temperature of −50° C. to −10° C., preferably −40° C. to −20° C.

Non-aqueous solvents include tetrahydrofuran (THF) and ethers, and THF is preferably employed.

In this reaction, the products can be obtained usually in the yield of 80% or more.

Grignard reagent [2] is prepared by A. Mendel's process [J. Organometal Chem., 6, 97 (1966)].

Compound [4] is prepared by reacting alcohol [3] in methoxypropene as a solvent at room temperatures, employing pyridinium-p-toluenesulfonic acid (PPTS) or p-toluenesulfonic acid (TsOH) as a catalyst. PPTS is preferably employed.

This reaction can usually be carried out quantitatively.

Compound [5] is prepared by reacting silylether [4] with tetrabutylammonium fluoride (n-Bu$_4$N$^+$F$^-$) in a non-aqueous solvent, preferably THF, at room temperatures to 60° C., preferably 30° C. to 40° C., and then removing silyl group. This preparation is carried out by conventional process.

In this reaction, the product can be obtained usually in the yield of 80% or more.

Compound [6] is prepared by oxidizing alcohol [5] with complex of sulfur trioxide and pyridine in dimethyl sulfoxide (hereinafter, may be referred to as DMSO) at room temperatures according to the process of J. R. Parikh et al. [J. Am. Chem. Soc., 89, 5505 (1967)].

Compound [8] is prepared by reacting aldehyde [6] with Wittig reagent [7] in anhydrous chloride.

In this reaction, the product can be obtained usually in the yield of 80% to 100%.

Compound [9] is prepared by reacting ester [8] in toluene, employing a reducing agent such as diisobutylaluminium hydride.

In this reaction, the product can be obtained usually in the yield of 90% or more.

Compound [12] is prepared by oxidizing alcohol [9] with complex of sulfur trioxide and pyridine in dimethyl sulfoxide, according to the said process of J. R. Parikh et al., and reacting aldehyde [10] obtained above with Wittig reagent [11] for 24 to 36 hours.

In this reaction, the product can be obtained usually in the yield of 64% or more.

Compound [13] is prepared by hydrolyzing ester [12] with 1.52N solution of lithium hydroxide in methanol and then reacting with acids.

In this reaction, the product can be obtained usually in the yield of 60% to 80%.

Trichostatin A [15] is prepared by oxidizing Compound [13] to obtain trichostatic acid [14] and then reacting trichostatic acid [14] with amine, in which hydrogen atom of hydroxyl group of hydroxylamine has been substituted by a protecting group.

The oxidation can be conducted in a medium such as methanol, benzene, glacial acetic acid and dioxane.

The preferred protecting groups include alkyl-substituted silyl, acetal, esters and acetyl.

In this reaction, trichostatic acid [14] and trichostatin A [15] can be obtained from Compound [13] usually in the yield of 30% to 50%

Aldehyde represented by the formula [1] is prepared by silylation and reduction of hydroxyisobutyric acid and then oxidizing with (COCl)$_2$ and triethylamine (TEA) in DMSO.

(1)

The present invention comprises the steps mentioned above, and consequently, optical active trichostatic acid and trichostatin A can be obtained by the present invention, said trichostatic acid and trichostatin A are each enantiomer.

Further, (S)-trichostatic acid has been become available, which was not available up to now.

EXPLANATION OF PREFERRED EMBODIMENTS

The present invention will be explained by the following examples.

The process comprises the following ten steps:
The first step: from starting material to Compound [3]
The second step: from Compound [3] to Compound [4]
The third step: from Compound [4] to Compound [5]
The fourth step: from Compound [5] to Compound [6]
The fifth step: from Compound [6] to Compound [8]
The sixth step: from Compound [8] to Compound [9]
The seventh step: from Compound [9] to Compound [12]
The eighth step: from Compound [12] to Compound [13]
The ninth step: from Compound [13] to Compound [14]
The tenth step: from Compound [13] to Compound [15]

In the steps, "IR", "NMR" and "optical rotations" was determined by means of "JASCO IR A-102", "JMN FX-100 (mfd. by JEOL, 100 MHz) and "JASCO DIP-140", respectively. Otherwise stated, $^1$H NMR spectra were recorded with TMS as an internal standard as CDCl$_3$ solution.

(1) The first step: From starting material to Compound [3]

Methyl hydroxyisobutyrate (starting material, $[\alpha]_D^{25}$ −26.1° (c=3.43 MeOH) having optical purity of 98% or more (10 g, 84.7 mmole) was stirred overnight together with t-butyldimethylsilylchloride (14 g, 93 mmole) and imidazole (12.7 g, 185 mmole) in 100 ml of dimethylformamide.

The mixture was treated with water, extracted with ether and then distilled to obtain 19.0 g of ester. (Yield 96.5%).

The properties of ester obtained are as follows:
(b.p. 108°-110° C./24 mmHg).
$n_D^{23}$ 1.4185.
$[\alpha]_D^{24} - 18.4°$ (c=2.02, CHCl$_3$).
IR $\nu_{max}^{film}$ 2950(s), 2350(s), 1740(s).
NMR δ ppm 0.08(6H, s), 0.90(9H, s), 1.15(3H, d, J=6.9 Hz), 2.67(1H, sextet, J=6.4 Hz), 3.70(3H, s), 3.65(1H, dd, J=9.3, 6.4 Hz), 3.75(1H, dd, J=9.3, 6.4 Hz).
Calcd. C 56.85%, H 10.41%; Found C 56.63%, H 10.32%.

Lithium borohydride (LiBH$_4$) (0.7 g, 32.1 mmole) was suspended in 50 ml of dried tetrahydrofuran, and ester (15 g, 64.5 mmole) obtained was dropped, cooling with ice, over 30 minutes, and then heated under reflux for 5 hours. The reaction mixture was cooled with ice, and to the mixture was added 15 ml of an aqueous solution of ammonium chloride, and then the mixture was extracted with ether. The extract was distilled (b.p. 105°-107° C./17 mmHg) to obtain 6.48 g of alcohol. (Yield 49.5%).

The properties of alcohol obtained are as follows:
$n_D^{23}$ 1.4274.
$[\alpha]_D^{23} - 10.8°$ (c=1.19, CHCl$_3$).
IR $\nu$max 3350(br), 2950(s), 2850(s), 1250(s).
NMR δ ppm 0.12(6H, s), 0.88(3H, d, J=6.9 Hz), 0.94(9H, s), 1.94(1H, m), 3.70(4H, m),
Calcd. C 58.76%, H 11.84%; Found C 58.55%; H 11.73%.

A solution of dimethylsulfoxide (5.3 g, 67.8 mmole) in 20 ml of methylene chloride was added dropwise into 40 ml of methylene chloride and oxalyl chloride (5.73 g, 45.2 mmole) in argon atmosphere at a temperature of −78° C. and the mixture was stirred for 15 minutes.

To the above mixture was added a solution of alcohol (obtained at −40° C. to −70° C.; 6.2 g, 30 mmole) in 20 ml of methylene chloride. After stirring the mixture for 15 minutes, triethylamine (13.7 g, 135 mmole) was added to the mixture, and the temperature was raised to 0° C. over about 30 minutes. After stirring the mixture at a temperature of 0° C. for 15 minutes, the temperature of the mixture was raised to room temperatures.

The reaction mixture was poured into ice-water and extracted with ether. After the extract was washed with water and brine, the extract was dried over magnesium sulfate and concentrated at not more than 40° C. to about 1/5 volume to obtain aldehyde of Compound [1].

This aldehyde was employed for the next reaction without carrying out purification.

Grignard reagent of formula [2] was prepared by reaction of magnesium (2.8 g, 118 mmole) with p-bromodimethylaniline (11.37 g, 56.8 mmole) in 60 ml of dried tetrahydrofuran. Aldehyde of Compound [1] and tetrahydrofuran (40 ml) were added to Grignard reagent (prepared above) with vigorous agitation at a temperature of not more than −35° C. After agitation for 10 minutes, a saturated aqueous solution of ammonium chloride was added to the mixture and the temperature thereof was raised to room temperatures. The mixture was extracted with ether and the extract was chromatographed over silicagel to obtain 7.48 g of alcohol of Compound [3].
(Yield 76.2%).

Data of Compound [3]
$n_D^{21}$ 1.5054.
$[\alpha]_D^{24} - 5.0°$ (c=1.14, CHCl$_3$).
IR $\nu$max 3450(br, m), 2950, 2860(s), 2800(m), 1610(s), 1520(s), 1080(s), 1020(m), 840(s).
NMR δ ppm 0.10(½6H, s), 0.12(½6H, s), 0.72(½3H, d, J=7.0 Hz), 0.85(½3H, d, J=7.0 Hz), 0.94(9H, s), 1.80-2.20(1H, m), 2.96(6H, s), 3.50-3.90(2H), 4.46(½1H, d, J=7.7 Hz), 4.84(½1H, d, J=3.7 Hz), 6.72(2H, d, J=9.3 Hz), 7.20(2H, d, J=9.3 Hz).
Calcd. C 66.82%, H 10.28%, N 4.33%; Found C 66.79%, H 10.31%, N 4.36%.

The data described above are data obtained from a mixture of diastereomer.

In the data, ½6H of NMR shows one of the signals which are to be obtained from two kinds of diastereomer.

(2) The second step: From Compound [3] to Compound [4]

Compound [3] (6.8 g, 21.0 mmole) was dissolved in 10 ml of methoxypropene (mfd. by Aldrich Chemical Company, Inc.), and to this solution was added 0.3 g of pyridinium p-toluenesulfonic acid, and the mixture was stirred at room temperatures for 3 hours.

After the reaction finished, a saturated aqueous solution of ammonium chloride was added, and the mixture was extracted with ether. The extract was chromatographed over silicagel to obtain 6.03 g of silyl ether of Compound [4].

Data of Compound [4]
$n_D^{23}$ 1.4866.
$[\alpha]_D^{22} - 6.05°$ (c=1.56, CHCl$_3$).
IR $\nu$max 2950(s), 2870(s), 1620(s), 1520(s).
NMR δ ppm 0.0(½6H, s), 0.08(½6H, s), 0.67(½3H, d, J=6.4 Hz), 0.90(½9H, s), 0.95(½9H, s), 1.00(½3H, d, J=6.4 Hz), 1.15(½6H, s), 1.36(½6H, s), 1.7-2.3(1H, m), 2.95(6H, s), 3.02(½3H, s), 3.05(½3H, s) 3.18(½1H, dd, J=6.5, 10 Hz), 3.48(2H, d, J=6.2 Hz), 3.55(½1H, dd, J=4.8, 10 Hz), 4.58(½1H, d, J=6.7 Hz), 4.69(½1H, d, J=6.7 Hz), 6.69(2H, d, J=8.7 Hz), 7.15(2H, d, J=8.7 Hz).
Calcd. C 66.79%, H 10.44%, N 3.54%; Found C 67.04%, H 10.21%, N 3.67%.

(3) The third step: From Compound [4] to Compound [5]

Compound [4] (5.23 g, 14.3 mmole) was dissolved in 30 ml of dried tetrahydrofuran (THF), and to this solution was added 15 ml of tetra-n-butylammonium fluoride in THF (1M, mfd. by Aldrich Chemical Company Inc.). The mixture was warmed to a temperature of 40° C. and stirred for 4 hours. A saturated aqueous solution of ammonium chloride was added to the mixture and the mixture was extracted with ether, the crude extract was chromatographed over silicagel to obtain 3.1 g of alcohol of Compound [5].
(Yield 76.3%).

Data of Compound [5]
$n_D^{19}$ 1.5050.
$[\alpha]_D^{24} - 8.71°$ (c=1.40, CHCl$_3$).
IR $\nu$max 3450(br), 2950(s), 1620(s), 1520(s), 1070(s), 1030(s).
NMR δ ppm 0.68(½3H, d, J=6.7 Hz), 0.72(½3H, d, J=6.7 Hz), 1.21(½6H, s), 1.40(½6H, s), 2.95(6H, s), 1.85-2.3(1H, m), 3.10(½3H, s), 3.18(½3H, s), 3.25-3.90(2-H+OH, m), 4.47(½1H, d, J=8.0 Hz), 4.80(½1H, d, J=4.3 Hz), 6.68(2H, d, J=8.7 Hz), 7.16(2H, d, J=8.7 Hz).

Calcd. C 68.29%, H 9.67%, N 4.98%; Found C 67.82%, H 9.60%, N 4.99%.

(4) The fourth step: From Compound [5] to Compound [6]

Compound [5] (2.38 g, 8.45 mmole) was mixed with 21.6 ml of dried dimethylsulfoxide and 7.5 ml of triethylamine, and to the mixture was added dropwise a solution of sulfur trioxide-pyridine complex (3.98 g, 25 mmole) in 21.6 ml of dimethylsulfoxide, while stirring, in argon atmosphere.

After stirring at room temperature for 5 to 120 minutes, the mixture was poured into ice-water and extracted with ehter. After the ether phase was washed with water and brine, and then dried over magnesium sulfate, the product was concentrated at not more than 40° C. to obtain aldehyde of Compound [6].

Compound [6] was employed for the next reaction without carrying out purification.

(5) The fifth step: From Compound [6] to Compound [8]

2(triphenylphosphoranylidene)propionate (7.6 g) was added to a solution of aldehyde of Compound [6] in 23 ml of dried methylene chloride, and the mixture was stirred under gentle reflux in argon atmosphere for 6 hours. After the reaction finished, the mixture was concentrated under reduced pressure, and then 10% ethyl acetate/n-hexane was added to the mixture. The precipitate produced was filtered and washed with 10% ethyl acetate/n-hexane. The filtrate was concentrated, and then the concentrated filtrate was chromatographed over silicagel to obtain 3.4 g of ester of Compound [8].

Data of Compound [8]

$n_D^{22}$ 1.5119.

$[\alpha]_D^{24}$ +31.3° (c=2.39, CHCl$_3$).

IR $\nu_{max}^{film}$ 3000(s), 1710(s), 1620(s), 1520(s), 750(m).

NMR δ ppm 0.79($\frac{1}{3}$3H, d, J=7.1 Hz), 1.02($\frac{1}{3}$3H, d, J=7.1 Hz), 1.07($\frac{1}{3}$3H, s), 1.10($\frac{1}{3}$3H, s), 1.26($\frac{1}{3}$3H, t, J=7.1 Hz), 1.29($\frac{1}{3}$3H, t, J=7.1 Hz), 1.30($\frac{1}{3}$3H, s), 1.38($\frac{1}{3}$3H, s), 1.78($\frac{1}{3}$3H, d, J=1.9 Hz), 1.88($\frac{1}{3}$3H, d, J=1.9 Hz), 2.60–2.95(1H), 2.94($\frac{1}{6}$6H, s), 2.96($\frac{1}{6}$6H, s), 3.06($\frac{1}{3}$3H, s), 3.12($\frac{1}{3}$3H), s), 4.00–4.32(2H), 4.42($\frac{1}{1}$1H, d, J=8 Hz), 4.51($\frac{1}{2}$, d, J=6 Hz), 6.50–6.73(1H), 6.65($\frac{1}{2}$2H, d, J=9.3 Hz), 6.68($\frac{1}{2}$2H, d, J=9.3 Hz), 7.12($\frac{1}{2}$2H, d, J=9.3 Hz), 7.15($\frac{1}{2}$2H, d, J=9.3 Hz).

Calcd. C 69.39%, H 9.15%, N 3.85%; Found C 69.41%, H 9.06%, N 3.88%.

(6) The sixth step: From Compound [8] to Compound [9]

Ester of Compound [8] (3.05 g, 8.39 mmole) was dissolved in 38 ml of dried toluene, and to this solution was added dropwise diisobutylaluminium hydride (n-hexane 1M solution, 20 ml, 20 mmole) in argon atmosphere at temperatures of −55° C. to −60° C. The mixture was stirred at a temperature of −78° C. for 30 minutes. After a saturated aqueous solution of Rochelle salt was added to the mixture, the temperature of the mixture was raised to room temperatures.

The mixture was filtered by using Celite (tradename: mfd. by Johns-Manville) to filter off a solid matter. The solid matter was washed with toluene exhaustively. The toluene layer collected was washed with a solution of Rochelle salt, and dried over magnesium sulfate, and then concentrated and chromatographed over silicagel to obtain 2.4 g of alcohol of Compound [9]. (Yield 89%).

Data of Compound [9]

$n_D^{19}$ 1.5271.

$[\alpha]_D^{24}$ −10.6° (c=2.32, CHCl$_3$).

IR $\nu_{max}^{film}$ 3400(br), 2950(s), 1620(s), 1520(s), 1070(s), 1020(s).

NMR δ ppm 0.80($\frac{1}{3}$3H, d, J=6.7 Hz), 1.00($\frac{1}{3}$3H, d, J=6.7 Hz), 1.08($\frac{1}{3}$3H, s), 1.10($\frac{1}{3}$3H, s), 1.32($\frac{1}{3}$3H, s), 1.38($\frac{1}{3}$3H, s), 1.52($\frac{1}{3}$3H, d, J=1.6 Hz), 1.65($\frac{1}{3}$3H, d, J=1.6 Hz), 2.60–3.00(1H), 2.93($\frac{1}{6}$6H, s), 2.96($\frac{1}{6}$6H), s), 3.08($\frac{1}{3}$3H, s), 3.10($\frac{1}{3}$3H, s), 3.50(—OH), 3.88($\frac{1}{2}$2H, d, J=5.2 Hz), 3.99($\frac{1}{2}$2H, d, J=5.2 Hz), 4.40($\frac{1}{1}$1H, d, J=6.5 Hz), 4.42($\frac{1}{1}$1H, d, J=6.5 Hz), 5.10($\frac{1}{1}$1H, d, J=7.5 Hz), 5.19($\frac{1}{1}$1H, d, J=6.5 Hz), 6.63($\frac{1}{2}$2H, d, J=8.6 Hz), 6.67($\frac{1}{2}$2H, d, J=8.6 Hz), 7.10($\frac{1}{2}$2H, d, J=8.6 Hz), 7.12($\frac{1}{2}$2H, d, J=8.6 Hz).

Calcd. C 70.99%, H 9.72%, N 4.36%; Found C 71.20%, H 9.57%, N 4.26%.

(7) The seventh step: From Compound [9] to Compound [12]

Alcohol of Compound [9] (1.86 g, 5.8 mmole) was oxidized with sulfar trioxide-pyridine complex (2.72 g, 17.1 mmole), dimethyl sulfoxide (30 ml) and triethylamine (7.5 ml) by the same procedure as that described in the fourth step (From Compound [5] to Compound [6]) to obtain aldehyde of Compound [10], which is employed in the next reaction step without carrying out purification.

Aldehyde of Compound [10] was dissolved in 20 ml of dried methylene chloride, and to the solution was added triphenylphosphoranylideneacetate (mfd. by Aldrich Chemical Company, Inc., 4 g, 12.0 mmol), and then the mixture was stirred under gentle reflux in argon atmosphere for 24 hours.

Further, phosphorane (1 g) was added to the mixture, and the mixture was heated under reflux for 12 hours to obtain 1.4 g of ester of Compound [12].

(Yield 64%).

Data of Compound [12]

$n_D^{19}$ 1.5264

$[\alpha]_D$ −6.76° (c=1.77, CHCl$_3$).

IR $\nu_{max}^{film}$ 3000 (m), 2950 (br), 1720 (s), 1620 (s), 1520 (s), 1070 (m), 1020 (s).

NMR δppm 0.84 ($\frac{1}{3}$3H, d, J=6.6 Hz), 1.01 ($\frac{1}{3}$3H, d, J=6.6 Hz), 1.08 ($\frac{1}{3}$3H, s), 1.10 ($\frac{1}{3}$3H, s), 1.32 ($\frac{1}{3}$3H, s), 1.37 ($\frac{1}{3}$3H, s), 1.69 ($\frac{1}{3}$3H, d, J=1.3 Hz), 1.78 ($\frac{1}{3}$3H, d, J=1.3 Hz), 2.94 ($\frac{1}{6}$6H, s), 2.96 ($\frac{1}{6}$6H, s), 3.05($\frac{1}{3}$3H, s), 3.08 ($\frac{1}{3}$3H, s), 3.74 ($\frac{1}{3}$3H, s), 3.75 ($\frac{1}{3}$3H, s), 4.43($\frac{1}{1}$1H, d, J=6.5 Hz), 4.48 ($\frac{1}{1}$1H, d, J=6.0 Hz), 5.60 ($\frac{1}{1}$1H, bd, J=10 Hz), 5.72 ($\frac{1}{1}$1H, bd, J=10 Hz), 5.74 ($\frac{1}{1}$1H, d, J=15 Hz), 5.80 ($\frac{1}{1}$1H, d, J=15 Hz), 6.12 ($\frac{1}{2}$2H, d, J=9.0 Hz), 6.65 ($\frac{1}{2}$2H, d, J=9.0 Hz), 7.07 ($\frac{1}{2}$2H, d, J=9.0 Hz), 7.10 ($\frac{1}{2}$2H, d, J=9.0 Hz), 7.25 ($\frac{1}{2}$2H, d, J=15 Hz), 7.32 ($\frac{1}{2}$2H, d, J=15 Hz).

Calcd. C 70.37%, H 8.86%, N 3.73%; Found C 70.18%, H 9.02%, N 3.64%.

(8) The eighth step: From Compound [12] to Compound [13]

Ester of Compound [12] (1.4 g, 3.73 mmole) was dissolved in 29.5 ml of methanol, and to the solution was added an aqueous solution of lithium hydroxide (0.52N, 9.85 ml, 5.12 mmole).

After the mixture was stirred at a temperature of 45° C. for 12 hours, the mixture was cooled to room temperatures, and the pH thereof was adjusted to 7 to 8 with 1N hydrochloric acid and the mixture was concentrated.

Water was added to the mixture and the pH of the mixture was adjusted to 3 to 4 with diluted hydrochloric acid, and then the mixture was stirred at room temperatures for 10 minutes.

The mixture was extracted with chloroform:methanol (95:5). The extract was washed with brine and dried over magnesium sulfate, and then the extract was concentrated to obtain 0.86 g of carboxylic acid of Compound [13].

(Yield 80%).

Data of Compound [13]

$[\alpha]_D^{20}$ +83° (c=0.355, CHCl$_3$: MeOH 9:1).

Softening point 135°–140° C., Light yellowish solid.

IR $\nu_{max}^{KBr}$ 3300 (br), 2900 (br), 1670 (s), 1620 (s), 1530 (m), 810 (m).

NMR δppm (CDCl$_3$/CD$_3$OD 9:1) 0.88 (½3H, d, J=6.7 Hz), 1.10 (½3H, d, J=6.7 Hz), 1.65 (½3H, brs), 1.80 (½3H, brs), 2.90 (½6H, s), 2.95 (½6H, s), 2.70–3.1 (1H), 4.40 (½1H, d, J=7.0 Hz), 4.45 (½1H, d, J=6.5 Hz), 5.70 (½1H, bd, J=10 Hz), 5.70 (½1H, d, J=15 Hz), 5.80 (½1H, d, J=15 Hz), 5.88 (½1H, bd, J=9.5 Hz), 6.72 (½2H, d, J=8.5 Hz), 6.75 (½2H, d, J=8.5 Hz), 7.15 (½2H, d, J=8.5 Hz), 7.18 (½2H, d, J=8.5 Hz), 7.18 (½1H, d, J=15 Hz), 7.37 (½1H, d, J=15 Hz).

Calcd. C 70.56%, H 8.01%, N 4.84%; Found C 70.19%, H 7.79%, N 4.78%.

(9) The ninth step: From Compound [13] to Compound [14]

Compound [13] (325 mg, 1.12 mmole) was dissolved in 5 ml of dried dioxane, and to the solution was added dropwise a solution of 300 mg of DDQ in 3 ml of dioxane. After the solution was stirred for 5 minutes at room temperatures, the precipitate produced was filtered off. The filtrate was concentrated, and then the residue was chromatographed over silicagel with benzene: isopropylalcohol to obtain Compound [14].

(Yield 34%).

Data of Compound [14]

IR$_{max}^{KBr}$ 2950 (br), 1680 (m), 1600 (s), 1370 (m).

NMR CDCl$_3$ δppm. 1.31 (3H, d, J=6.8 Hz), 1.92 (3H, brs), 3.07 (6H, s), 4.40 (1H, dq, J=9.6, 6.8 Hz), 5.81 (1H, d, J=15.6 Hz), 6.09 (1H, brd, J=9.6 Hz), 6.64 (2H, d, J=8.8 Hz), 7.38 (1H, d, J=15.6 Hz), 7.89 (2H, d, J=8.8 Hz).

Calcd. C 71.06%, H 7.37%, N 4.87%; Found C 70.72%, H 7.50%, N 4.71%.

m.p. 89°–90° C., $[\alpha]_D$ +138° [(R)-isomer], −131° [(S)-isomer)].

The product was identified as trichostatic acid.

It was determined by analysis, employing CHIRALCEL OB (mfd. by Daicel Chemical Industries, Ltd.), that optical purities of (R)- and (S)-isomers were 98% or more.

(10) The tenth step: From Compound [13] to Compound [15]

Trichostatic acid of Compound [14] (48 mg, 0.17 mmole) obtained as above from Compound [13] as dissolved in 500 μl of dried toluene. The solution was added to a mixture of DCC (dicyclohexylcarbodiimde) and o-methoxypropylhydroxylamine (350 mg, 3.34 mmole), and the mixture obtained was stirred at a temperature of 0° C. for 30 minutes. Water was added to the mixture, and the mixture was extracted with ethyl acetate. The extracted crude product was allowed to react with acetic acid in 70% solution of acetic acid at a temperature of 40° C.

The pH of the reaction product was adjusted to 6.5 by adding an aqueous solution of sodium bicarbonate and the product was extracted with ethyl acetate, and then the extract was purified by thin layer chromatography to obtain 12 mg of Compound [15].

(Yield 24%).

Physical properties of Compound [15] are as follows: $[\alpha]_D^{23}$ −41° C. (C=0.08, EtOH) was shown. In $^{13}$C-NMR, the signals were shown in 12.4 ppm, 17.8, 39.9, 41.1, 111.2, 116.0, 123.8, 131.1, 133.2, 141.9, 145.3, 154.3, 165.7, 200.1 (CDCl$_3$/CD$_3$OD 5:1). These figures agree closely with those of natural products.

Therefore, Compound [15] was determined to be trichostatin A and optical active matter.

In the above examples, (R)-methyl hydroxyisobutyrate was used as a starting material, and data of (R)-isomer were shown. Optical rotations of (S)-isomers are shown in the followings, which were obtained when (S)-methyl hydroxyisobutyrate was used and the same procedure as that mentioned above was repeated. In NMR and IR, identical figures were obtained.

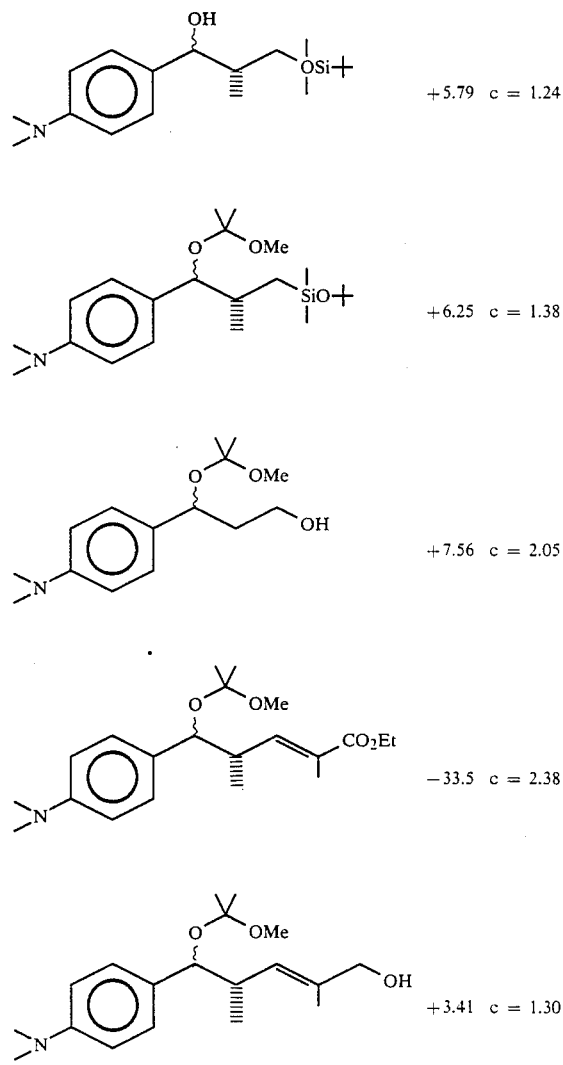

-continued

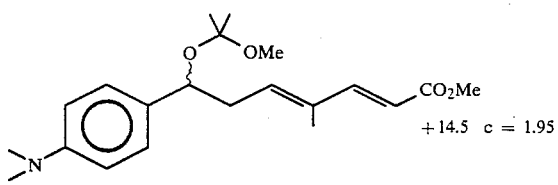

+14.5  c = 1.95

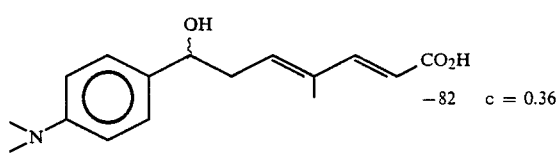

−82  c = 0.36

-continued

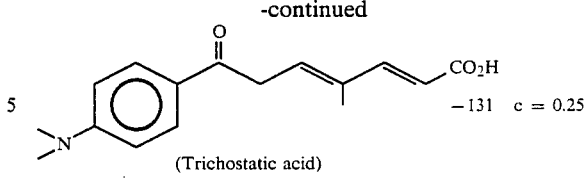

−131  c = 0.25

(Trichostatic acid)

What we claim is:
1. (E,E)-7-(4'-dimethylaminophenyl)-7-hydroxy-4,6-dimethylhepta-2,4-dienoic acid represented by the following formula [13]:

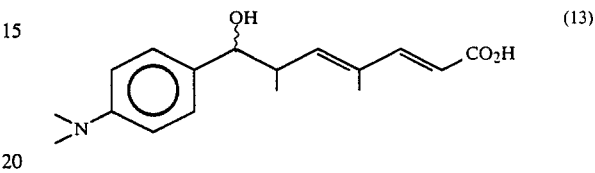

(13)

2. (E,E)-7-(4'-dimethylaminophenyl)-7-hydroxy-4,6-dimethyl-hepta-2,4-dienoic acid as claimed in claim 1 wherein said acid is (2E,4E,6R)-7-(4'-dimethylaminophenyl)-7-hydroxy-4,6-dimethyl-hepta-2,4-dienoic acid or (2E,4E,6S)-7-(4'-dimethylaminophenyl)-7-hydroxy-4,6-dimethyl-hepta-2,4-dienoic acid.

* * * * *